United States Patent [19]

Keck et al.

[11] Patent Number: 5,330,902

[45] Date of Patent: Jul. 19, 1994

[54] LEADER SEQUENCES FOR THE PRODUCTION OF RECOMBINANT PROTEINS

[75] Inventors: Peter C. Keck, Millbury; Charles M. Cohen, Medway; James S. Huston, Newton; Richard J. Ridge, Acton, all of Mass.

[73] Assignee: Creative BioMolecules, Inc., Hopkinton, Mass.

[21] Appl. No.: 3,989

[22] Filed: Jan. 15, 1993

Related U.S. Application Data

[60] Division of Ser. No. 857,684, Mar. 25, 1992, Pat. No. 5,215,896, which is a continuation of Ser. No. 731,303, Jul. 16, 1991, abandoned, which is a continuation of Ser. No. 28,500, Mar. 20, 1987, abandoned.

[51] Int. Cl.$^5$ .................... C12N 15/62; C12N 15/09; C07K 3/24
[52] U.S. Cl. ................. 435/69.7; 435/69.1; 435/172.3; 935/8; 935/10; 935/47
[58] Field of Search .................. 435/69.7, 69.1, 172.3; 935/8, 10, 47

[56] References Cited

U.S. PATENT DOCUMENTS

| | | | |
|---|---|---|---|
| 4,366,246 | 12/1982 | Riggs | 435/69.8 |
| 4,425,437 | 1/1984 | Riggs | 435/320.1 |
| 4,431,739 | 2/1984 | Riggs | 435/253 |
| 4,543,329 | 9/1985 | Daum et al. | 435/69.1 |
| 4,563,424 | 1/1986 | Riggs | 435/69.4 |
| 4,743,679 | 5/1988 | Cohen et al. | 530/350 |
| 4,751,180 | 6/1988 | Cousens et al. | 435/69.7 |
| 5,004,686 | 4/1991 | Cohen et al. | 435/69.7 |
| 5,013,653 | 5/1991 | Huston et al. | 435/69.7 |

FOREIGN PATENT DOCUMENTS

| | | |
|---|---|---|
| 0035384 | 9/1981 | European Pat. Off. |
| 0047600 | 3/1982 | European Pat. Off. |
| 0117058 | 8/1984 | European Pat. Off. |
| 0117059 | 8/1984 | European Pat. Off. |
| 0150126 | 7/1985 | European Pat. Off. |
| 0161937 | 11/1985 | European Pat. Off. |
| 0163573 | 12/1985 | European Pat. Off. |
| WO84/03103 | 8/1984 | PCT Int'l Appl. |
| WO84/04756 | 12/1984 | PCT Int'l Appl. |
| WO85/03079 | 7/1985 | PCT Int'l Appl. |
| 2140810A | 12/1984 | United Kingdom. |

OTHER PUBLICATIONS

Epand, Richard M., (1983) The amphipatic helix: its possible role in the interaction of glucagen and other peptide hormones with membrane receptor sites *TIBS*, 8(6):67–69.

Blanc, et al. (1983) Examination of the requirements for an amphiphilic hilical structure in $\beta$-endorphin through the design, synthesis and study of model peptides. *Journ. of Bio. Chem.*, 258(13):8277–8284.

Taylor, et al. (1983) Characterization of an amphiphilic helical structure in $\beta$-endorphin through the design, synthesis and study of model peptides. *Journ. of Bio. Chem.*, 258(7):4464–4471.

(List continued on next page.)

*Primary Examiner*—Christopher S. F. Low
*Assistant Examiner*—Rebecca Prouty
*Attorney, Agent, or Firm*—Testa, Hurwitz & Thibeault

[57] ABSTRACT

Disclosed is a novel polypeptide useful as a leader or trailer peptide moiety in recombinant DNA protein production techniques involving fused protein methodology. The polypeptide comprises an amphiphilic helix designed at the DNA level to have hydrophilic charged amino acid residues on one side of the barrel of the helix and nonpolar amino acid residues on the other side of the barrel of the helix. When DNA encoding the helix is attached to a gene encoding a protein of interest, high level expression is achieved and inclusion bodies are spontaneously formed. The inclusion bodies may be collected and purified easily by altering the ionic strength and/or pH of media used to dissolve the inclusion bodies. After purification, the fused protein is cleaved to separate the amphiphilic helix from the product.

10 Claims, 4 Drawing Sheets

OTHER PUBLICATIONS

Shoemaker, et al. (1985) *Proc. Natl. Acad. Sci. USA*, 82:2349-2353.

Brewer and Sassenfeld, "The purification of recombinant proteins using C-terminal polyargineni fusions." *Trends In Biotechnology*, (1985) vol. 3, No. 5, 119-122.

Uhlen, et al. (1983) *Gene*, 23:369-378.

Germino, et al. (1983) *Proc. Natl. Acad. Sci. USA*, 80:6848-6852.

Sassenfeld and Brewer, "A polypeptide fusion designed for the purification of recombinant proteins". (1984) *Biotechnology*, Jan. 1984, pp. 76-81.

Nagai, et al. (1984) *Nature*, 309:810-812.

Germino, et al. (1984) *Proc. Natl. Acad. Sci. USA*, 81:4692-4696.

DeGrado et al., J. American Chemical Soc., vol. 103, No. 3, 1981, pp. 679-681.

Ho et al., J. American Chemical Soc., vol. 109, No. 22, 1987 pp. 6751-6758.

Lau et al., J. Biological Chemistry vol. 259, No. 21, pp. 13253-13261; 1984.

Fukushima et al., J. Am. Chem. Soc. 101:3703 (1979).

Moe et al., Amer. Chem. Soc. 24:1972 (1985).

Musso et al., Biochem. Biophys. Res. Comm. 119:713 (1984).

Yokoyama et al., J. Biol. Chem. 225:7333 (1980).

Ginger E. et al., Nature, 330:670-672, Dec. 1987.

Marston, F. A., Review Article, Biochem. J. 240:1-2, 1986.

Kaiser, E. T., et al., Amphiphilic Secondary Structure: Design of Peptide Hormones, Science, 223, pp. 249-255, 1987.

Chou, P. Y., et al., "Empirical Predictions of Protein Conformation", Ann. Rev. Biochem., 47:251-76, 1978.

Sung, N. L., et al., Short Synthetic Oligodeoxyribonucleotide Leader Sequences Enhance Accumulation of Human Proinsulin Synthesized in *Escherichia coli*, PNAS, USA, 83:561-565, 1986.

Lau, S. H. et al., Surface Properties of an Amphiphilic Peptide Hormone and of its Analog: Corticotropin-releasing Factor and Sauvagine, PNAS, USA, 80: pp. 7070-7074, Dec. 1983.

LEADER SEQUENCES FOR THE PRODUCTION OF RECOMBINANT PROTEINS

CROSS REFERENCE TO RELATED APPLICATIONS

This is a divisional application of copending application Ser. No. 07/857,684 filed on Mar. 25, 1992, and now U.S. Pat. No. 5,215,896 issued Jun. 1, 1993, which is a continuation of application Ser. No. 07/731,303 filed on Jul. 16, 1991, now abandoned, which is a continuation of application Ser. No. 07/028,500 filed on Mar. 20, 1987, now abandoned.

BACKGROUND

This invention relates to the production and purification of polypeptides produced using genetic engineering techniques. More particularly, it relates to genetically engineered fused polypeptides including a novel alpha helical amphiphilic amino acid sequence useful in promoting high expression and in isolating and purifying the fused product.

Advancements in recombinant DNA technology permitting foreign genes to be incorporated into various cells have made possible the expression of products foreign to the cell. The protein of interest will often be degraded by intracellular enzymes, and it may be difficult to separate it from other materials expressed by or comprising the structural materials of the host organism. Protection from intracellular degradation can be achieved by fusing a sequence of amino acids to the target protein to avoid digestion by enzymes within the cell. In addition, the fused protein can be designed to facilitate isolation and purification if the desired protein is fused to a polypeptide having characteristics exploitable in purification.

The fusion product is encoded by DNA comprising the gene coding for the protein of interest linked to a DNA sequence encoding a polypeptide other than the protein of interest. Fusion methodology generally has been discussed at length in the prior art. For example, European Patent Application No. 0047600 is understood to disclose a process for synthesizing bovine growth hormone by producing a fusion protein and purifying the growth hormone from the culture medium of the host organism. Other proteins have been produced through fusion techniques.

Generally, the prior art teaches that genetic material encoding a cleavage site can be incorporated between the DNA encoding the desired protein and the DNA encoding the additional fused material. Expression yields a precursor protein comprising the amino acid sequence of the target polypeptide linked to one or more amino acids defining a selected cleavage site and another amino sequence. See, for example, EPO 0035384, EPO 0161937, and EPO 0163573.

The fusion product can also comprise a moiety designed to facilitate its isolation. For instance, see PCT/84/03103 and U.S. Pat. No. 4,431,739.

It is an object of this invention to provide a method for the production, isolation, and purification of genetically engineered proteins. Another object is to provide a method for obtaining recombinant protein of interest in improved yields. Another object is to provide a method which can be adapted to any polypeptide of interest which can be coded for and expressed by a host organism. Another object is to provide a novel family of leader sequences which induce high levels of expression, which cause the fused polypeptide product it comprises to form insoluble aggregates (inclusion bodies) in the cellular host, and which permit resolubilization and purification of the fused polypeptide. Still another object is to provide such a procedure which is both efficient and inexpensive.

These and other objects of the invention will be apparent from the description, drawing, and claims that follow.

SUMMARY OF THE INVENTION

Broadly, the invention features a method of promoting the spontaneous formation of insoluble aggregates or inclusion bodies rich in a target polypeptide of interest within a recombinant host cell capable of expressing the target polypeptide. The invention provides, in its various aspects, a fused protein expressable by recombinant DNA in a transformant, the recombinant DNA encoding the fused protein, and methods of producing polypeptides of interest using these reagents. The fused protein comprises a target polypeptide linked to a pendant polypeptide, which may be either a leader or trailer sequence (attached at either the amino or carboxyl terminus of the target, respectively), and which, in aqueous solution, has an amphiphilic alpha helical structure having a central axis and opposed hydrophilic and hydrophobic lateral surfaces. The hydrophobic surface comprises axially and circumferentially proximate nonpolar amino acid residues disposed on the barrel of the helix. The hydrophilic surface comprises axially and circumferentially proximate charged amino acid residues.

When used as a leader sequence in procaryotic cell expression systems, the DNA encoding the amphiphilic helix induces high expression levels, i.e., results in production of fused polypeptide at levels at least comprising ten percent of the total expressed protein of the cell, typically 30 to 40 percent, and occasionally as high as 50 percent. The fused protein is characterized by the ability to spontaneously form insoluble aggregates within the host cell organism in which it is expressed, and thereby facilitates production and isolation of the product.

In preferred embodiments, the pendant polypeptide of the fused protein is a proline-free polypeptide of the structure:

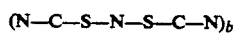

$$(N-C-S-N-S-C-N)_b$$

wherein each N is a nonpolar amino acid residue, each C is a charged amino acid residue, each S is a neutral amino acid residue, b is an integer from 1-30, and up to two of the amino acid residues in each repeating segment may be histidine. The charged amino acid residues together define the hydrophilic surface and the nonpolar amino acid residues together define the hydrophobic surface when the polypeptide assumes its helical conformation.

Preferred nonpolar, charged, and joining residues are determined by both the type of residue, e.g., N, C or S, and by its helix forming ability as defined in the literature on protein secondary structure and set forth in Table 1.

TABLE 1

Amino Acid Residue Preference as a Function of Alpha Helix Forming Tendency

| Residue Group: | | | | | |
|---|---|---|---|---|---|
| N | | C | | S | |
| Met | 1.45[1] | Glu(−) | 1.51 | Gln | 1.11 |
| Ala | 1.42 | Lys(+) | 1.16 | His | 1.00 |
| Leu | 1.21 | Asp(−) | 1.01 | Thr | 0.83 |
| Phe | 1.13 | His(+) | 1.00 | Ser | 0.77 |
| Trp | 1.08 | Arg | 0.98 | Asn | 0.67 |
| Ile | 1.08 | | | | |
| Val | 1.06 | | | | |
| His | 1.00 | | | | |
| Gly | 0.57 | | | | |

[1] Helix forming tendency as defined in the protein secondary structure literature by Fasman and Chou (Ann. Rev. Biochem. 1978, 47:251-76). Below the value of 1.00, residues tend to disrupt helical regions.

Preferred nonpolar residues for use in the alpha helical amphiphilic structure include methionine, alanine, leucine, phenylalanine, tryptophan, isoleucine, and valine. From this set, alanine and leucine are preferred due to steric packing considerations during helix-helix aggregation. Preferred charged residues include glutamic acid, lysine, and aspartic acid. The preferred side residue, designated S in the above-referenced formula, is glutamine. Asparagine has been used although it is a poor helix former. In general, provided the bulk of the helix is comprised of known good helix formers, a residue that is a poor helix former can be tolerated. This is not the case, however, with proline which is known to interrupt helical regions.

In many instances, it is preferred that each 7 amino acid segment of the helix contain both an anionic amino acid and a cationic amino acid so that the hydrophilic surface on one side of the barrel of the amphiphilic helix has a net neutral charge. In other instances, particularly where the target polypeptide comprises amino acid residues which collectively impart a net charge to the target polypeptide, the charged groups in one or more of the segments in the helix are selected to be of the opposite charge so that, on balance, the fused protein is neutral. In addition, placement of negative charge groups at the N-terminal (+) end and positive charge groups at the C-terminal (−) end of the polypeptide result in the formation of dipole moments across the peptide bonds along the helix, thus promoting helix stability (Shoemaker et al., 1985, Proc. Natl. Acad. Sci. USA, 82:2349-2353).

Histidine may be used in various locations in the helix segments as it takes a charged, cationic form in acidic or neutral solutions and is neutral in basic solutions. Charged histidine is also hydrophilic. A histidine-containing oligomer of the helix can form inclusion bodies which can be purified easily. For example, sequential passage of a solution of dissolved inclusion bodies through ion exchange media at two different pHs can result in significant concentration of fused protein.

The method of the invention involves inserting DNA encoding and capable of expressing the fused protein into a cellular host, permitting the host to express the fused protein in the form of inclusion bodies, separating the inclusion bodies from the cellular host, and then cleaving the fused protein to release the target polypeptide.

When the leader of the fused protein contains His, the fused protein may be advantageously separated from diverse other proteins in the cell by dissolution of the inclusion bodies in media having a second different ionic strength or different pH.

The tendency for aggregation of neutral amphiphilic helices is enhanced in high ionic strength media due to increased interaction of the hydrophobic surfaces, and in low ionic strength media due to increased interaction of the hydrophilic charged surfaces. The ability to change the total charge of His-containing helices by varying pH modifies both of these aggregation effects. The solubility of the histidine-containing helices often is pH dependent.

The currently preferred helical structures comprise the following amino acid sequences:

(Ala-Lys-Asn-Leu-Asn-Glu-Ala)$_d$;
(Ala-Lys-Gln-Leu-His-Asp-Ala)$_d$;
(Ala-His-Asn-Leu-Asn-Glu-Ala)$_d$ and;
(Ala-Lys-Gln-His-Gln-Glu-Ala)$_d$, wherein d is an integer from 1 to 10.

Other advantages and features of the invention will be apparent from the description, drawing, and claims which follow.

Figure 1:
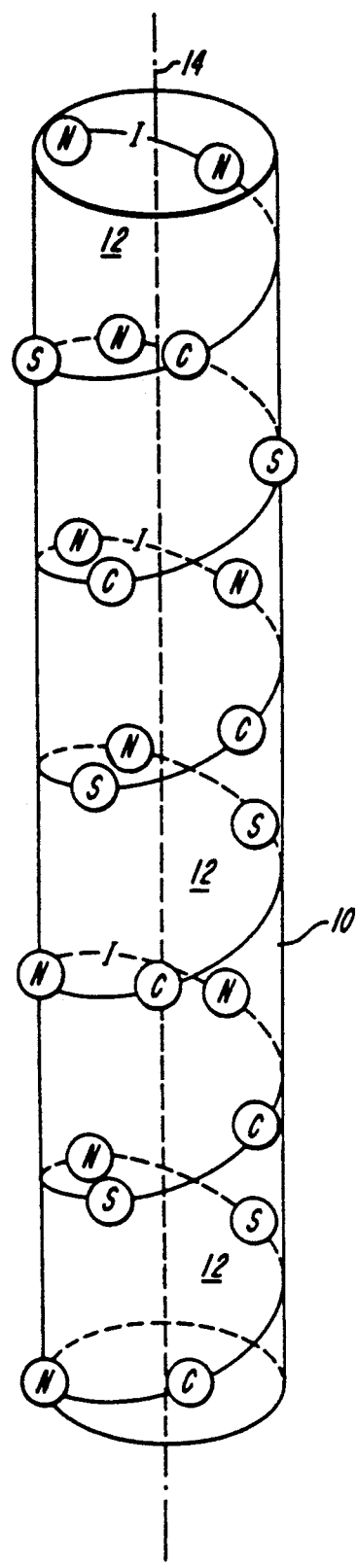
FIG. 1 is a schematic illustration of the secondary structure of the amphiphilic helix of the invention useful in explaining its properties.

∇—10mM phosphate, sodium ion variable from 10mM to 20mM;

△—10mM acetate, sodium ion variable from 5.3mM to 9.5mM;

○—10mM phosphate, 10mM acetate, sodium ion variable from 0mM to 20mM;

+—0.5 mM phosphate, 5mM pyrophosphate, sodium ion variable from 10mM to 20mM;

□—5mM phosphate, 5mM pyrophosphate, 20mM sodium ion, acetate ion variable from 12mM to 0.8mM.

DESCRIPTION

The production of various proteins of interest has heretofore been achieved by expressing in host cells a fused protein which is collected, purified, and then cleaved to remove the extraneous portion of the molecule. This invention constitutes an improvement and unobvious refinement of this general method. The process of the invention generally involves the engineering of a recombinant DNA which, upon expression in a suitable host, e.g., prokaryotic cells such as E. Coli, produces a fused polypeptide in abundance. The fused polypeptide, among other advantageous properties, spontaneously forms intracellular inclusion bodies in the host cell organism. Also, the fused polypeptide may be designed to be efficiently cleaved by virtue of other properties of the molecule discussed below.

This invention is based on the concept that the intracellular stability and ease of collection of fused protein could be improved if the polypeptide of interest were linked, preferably at its amino terminal end, directly or through a linking sequence, to a pendant polypeptide having unique properties. Specifically, the pendant polypeptide could induce high level expression, promote the formation of insoluble inclusion bodies within the producing host cell, and be exploited to aid in purification of the fused protein prior to cleavage. The general approach of the invention involves construction of recombinant DNA which encodes a fused polypeptide, which, upon expression, results in expression of an amphiphilic alpha helical polypeptide structure linked to a target protein, i.e., a protein of interest having potential or demonstrable utility. The DNA thus is designed to encode a sequence of amino acids which, when expressed and disposed in aqueous solution, forms a preferably well defined alpha helix. The helix preferably comprises one or more units or segments, each of which comprise seven amino acids of the general structure NCSNSCN. The letter N refers generically to nonpolar, hydrophobic amino acid residues; the letter C refers generically to charged, hydrophilic amino acid residues; and the letter S refers to side amino acid residues.

Each segment of this type of helix structure thus has three nonpolar residues and two charged residues. Alternatively, the helix can have the structure CNSCSNC, in which case each segment has two nonpolar residues and three charged residues. Such a structure has increased hydrophilic character relative to the preferred NCSNSCN sequence, and this property can have advantages in imparting solubility to inherently water-insoluble target proteins. If desired, different segments of the helix may comprise a different specific amino acid sequence. Of course, the generic formulas of the helices of the invention could also be represented with a "phase shifted" designation. Thus, helices represented, for example, by the formulas CSNSCNN, or SNSCNNC are the equivalent to the preferred structure designation disclosed herein. Also, while it is preferred that each C in each segment comprise a charged amino acid, and each N a nonpolar amino acid, occasional substitutions of other types of amino acids are permissible provided the substitute amino acids are reasonably good helix formers and thus do not significantly alter the pendant polypeptide's alpha helical structure.

When the protein assumes its secondary configuration, the result is an alpha helix having opposed surfaces of different character. One surface comprises proximate charged residues, thereby imparting hydrophilic properties to that side of the barrel of the helix. The opposite side comprises proximate hydrophobic amino acid residues, thereby imparting hydrophobic properties to the opposite surface. The joining or S (side) residues are preferably uncharged, hydrophilic amino acids whose primary function is to link the hydrophobic and hydrophilic lateral surfaces of the helix.

Histidine (His) is unique among the amino acids in that, depending on the media in which it is disposed, it can be cationic or neutral. It can be used in place of the central nonpolar residue in the seven amino acid segment constituting the helix, as a charged group, as a side group, or not at all, depending on the desired properties of the helix. In acidic media, the histidine residue accepts a proton and becomes positively charged and hydrophilic. In basic media, the histidine residue remains neutral and becomes somewhat hydrophilic. The use of His in the helix structure enables one to alter the net charge and solubility of individual helix molecules by changing the pH of the solution.

The general structure of the helix is depicted in FIG. 1. As illustrated, the helix may be visualized as winding about a cylinder or "barrel" 10. The winding consists of a chain of amino acids labelled N, C, and S as set forth above. The structure of the protein is such that on the cross hatched surface 12 of the cylinder 10, only C or S residues appear, whereas, on the opposite surface, only N or S residues appear, and in general, the S residues are disposed between one surface, dominated by the C or charged residues, and the other surface, dominated by N or nonpolar residues.

Figure 2:
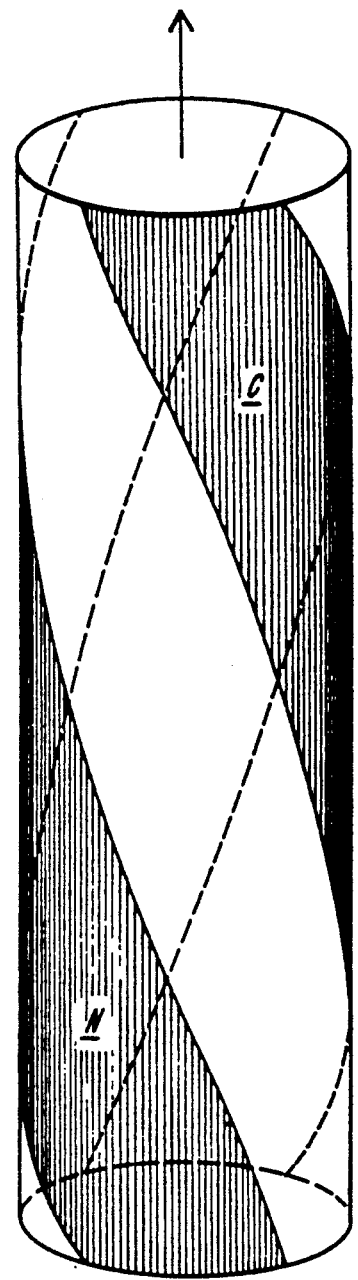
FIG. 2 is a schematic illustration of the helix of FIG. 1 illustrating the nonpolar and polar surfaces of the helices of the invention.

The effect of using the seven amino acid segment as a repeating unit is to obtain minimal rotation about the barrel's central axis 14 of the charged, hydrophilic surface (defined by charged amino acid residues adjacent in space on the helix), and of the nonpolar surface defined by the adjacent spacial location of the nonpolar residues. Thus, the amino acids defining the hydrophilic charged surface and the amino acids defining the non polar surface are always disposed on opposite sides of the barrel of the helix as shown schematically in FIG. 2, although due to the geometry of the alpha helix, both surfaces have a slight left helical twist.

The preferred nonpolar residues for use in the helix are phenylalanine (Phe), leucine (Leu), alanine (Ala), and tryptophan (Trp). Isoleucine (Ile), valine (val) and methionine (Met) may also be used. Proline (Pro) is also nonpolar, but has a side chain which loops back to reattach to the main chain, forcing a bend in the main chain, and eliminating the proton on its peptide bond nitrogen (which is necessary for hydrogen bonding to occur), thereby disrupting alpha helical structure. Accordingly, it is preferably not used in the structure of the helix. The hydrophilic amino acids useful in construction of the helix include the anionic amino acids glutamic acid (Glu) and aspattic acid (Asp) and the cationic amino acid lysine (Lys), which is preferred over arginine (Arg). As side groups useful in constructing the helix, asparagine (Ash), and glutamine (Gln) are preferred. Cysteine (Cys) is also a useful hydrophilic amino acid but it is not normally employed as a side group because of its potential for forming disulfide bonds, thus potentially disrupting the helical structure and complicating cleavage and purification of the final product.

The design of the helix is such that in high ionic strength media, e.g., aqueous solutions containing relatively large concentrations of charged species, the hydrophobic surfaces of helices in separate molecules interact to form micelles. Conversely, in low ionic strength media, ionic or hydrostatic interactions dominate and aggregates are again formed. Between these extremes lie conditions in which the fused protein is soluble.

The use of histidine as an S amino acid when one C is a cationic amino acid and the other is anionic, results in a helix which has a net positive charge at low pH, and accordingly is inhibited from forming aggregates by electrostatic repulsion. As the pH increases, e.g., pH greater than 7, the histidine moiety loses a hydrogen ion and becomes neutral. The helix then has a net neutral charge permitting formation of hydrophobic aggregates. Such a helix expressed in an E. coli cell will result in the formation of inclusion bodies in the intracellular pH range, e.g., 7.6. These may be collected and disposed in an acidic medium e.g., at pH 5, where the fused protein will dissolve thereby facilitating additional treatment steps including cleavage.

The number of units of the helix used in a particular case is determined empirically by considering the size and solubility characteristics of the target polypeptide. Generally, a sufficient number of units should be used to assure that the solubility properties of the helix dominate. For example, a large, substantially neutral target protein for best results would be linked to a helix comprising at least 10 segments. Conversely, smaller proteins comprising, for example, 50 amino acids require fewer repeat units.

Another consideration in the helix construction relates to the effect of ionic repulsion among individual helices. In most cases, it is preferred that one of the charged amino acids be anionic and the other be cationic such that the net charge is neutral. As noted above, the charge characteristics can be made pH dependent by the introduction of histidine. The exception to this general rule arises in the situation where the target protein itself has a significant net charge. In this case, intracellular formation of inclusion bodies can be fostered by designing a helix containing charged groups which neutralize the charge on the target protein by appropriate selection of the C residues.

Figure 3:
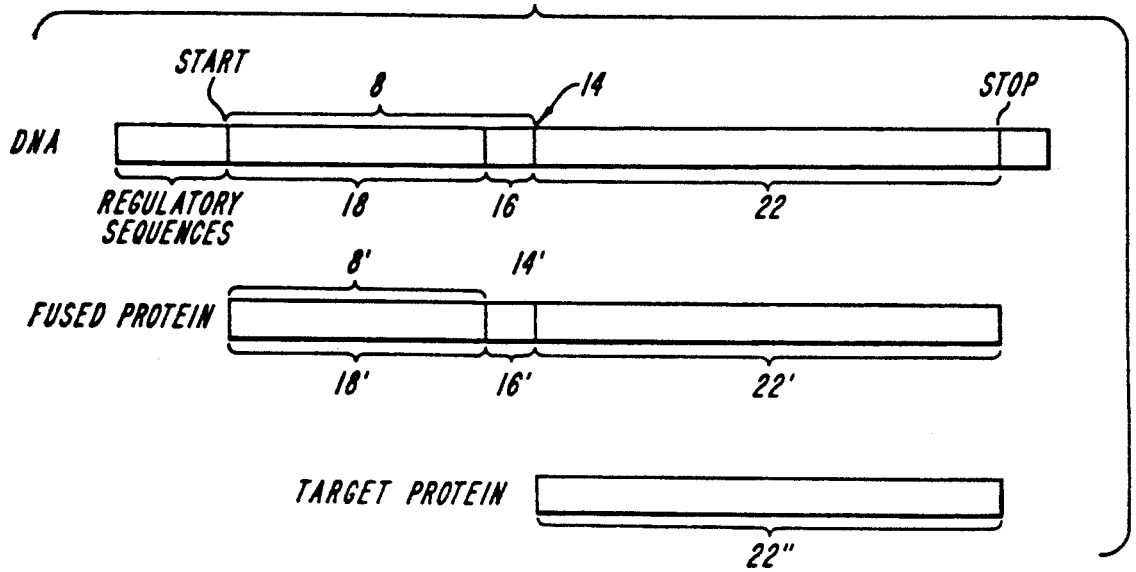
FIG. 3 is an illustration of the structure of the fused DNA, fused protein, and target protein product showing the sequence of events occurring at the molecular level during the practice of the invention.

The overall structure of the preferred DNA of the invention, the fusion protein it encodes, and the resulting target peptide product are schematically illustrated in FIG. 3. Reference characters in the DNA are carried over into the protein as corresponding primed characters. The DNA is composed of two distinct nucleotide sequences linked together. The first sequence encodes a polypeptide, most or all of which will ultimately be discarded. Linked to the 3' or 5' terminus of the first sequence is DNA encoding a target polypeptide— the protein of interest, which ultimately will be harvested. In the drawing, 3' of the regulatory sequences is a first DNA sequence 8 comprising nucleotides encoding three subsequences: 1) a sequence 18 comprising the amphiphilic helix of the invention described above, a sequence referred to herein as a "hinge" or "hinge region" 16, and an amino acid or amino acid sequence defining a cleavage site 14. DNA encoding additional amino acid sequence (not shown) may also be included. Attached to the DNA encoding cleavage site 14 is DNA encoding the protein of interest 22.

The encoded fused protein comprises the pendant amphiphilic helix 18', a hinge region 16', a cleavage site 14', and the target protein 22'. After collection and purification of the fused protein, optionally exploiting the properties of the helix 18', the fused protein is cleaved at the cleavage site 14' to yield the product 22". The hinge 16' and cleavage site 14', like the helix 18', are incorporated by engineering the DNA. The function of the cleavage site 14' is to serve as a site of action for a preselected cleavage agent. The function of the hinge region 16' is to improve the rate and/or the specificity of the cleavage reaction.

The processes for manipulating, amplifying, and recombining DNA which encode amino acid sequences of interest are generally well known in the art, and therefore, not described in detail herein. Methods of identifying and isolating genes encoding proteins of interest, or for constructing such genes, are well understood and developed. These processes are described in the patent and other literature. See, for example, U.S. Pat. No. 4,431,739. In general, the methods involve selecting genetic material coding for amino acids which define the polypeptide of interest according to the genetic code.

Accordingly, the DNA construction principle disclosed herein can be exploited using known construction techniques involving the use of various restriction enzymes which make sequence specific cuts in DNA to produce blunt ends or cohesive ends, DNA ligases, techniques enabling enzymatic addition of sticky ends to blunt-ended DNA, construction of synthetic DNAs by assembly of short oligonucleotides, cDNA synthesis techniques, and synthetic probes for isolating genes having a particular function. Various promoter sequences and other regulatory DNA sequences used in achieving expression, and various types of host cells are also known and available. Conventional transfection techniques, and equally conventional techniques for cloning and subcloning DNA are useful in the practice of this invention and known to those skilled in the art. Various types of vectors may be used such as plasmids and viruses including animal viruses and bacteriophages. The vectors may exploit various marker genes which impart to a successfully transfected cell a detectable phenotypic property that can be used to identify which of a family of cells has successfully incorporated the recombinant DNA of the vector. Given the foregoing state of the genetic engineering art, skilled persons are enabled to practice the invention disclosed herein in view of this disclosure.

One method for obtaining DNA encoding the various helix structures disclosed herein is by assembly of synthetic oligonucleotides in a conventional, automated, polynucleotide synthesizer followed by ligation with appropriate ligases. For example, overlapping, complementary DNA fragments comprising 15 bases may be synthesized using phosphoramidite chemistry, with end segments left unphosphorylated to prevent polymerization during ligation. One end of the synthetic DNA is left with a "sticky end" corresponding to the site of action of a particular restriction endonuclease, and the other end left with an end corresponding to the site of action of another restriction endonuclease. Alternatively, the DNA encoding the helix may be created by synthesizing longer single strand fragments (e.g., 50-100 nucleotides long) in, for example, a Biosearch oligonucleotide synthesizer, and then annealing the fragments.

As represented in FIG. 3, the hinge region 16' is encoded by a DNA segment 16. The expressed hinge region 16' is preferably an unstructured segment adjacent or about the cleavage site 14' comprising at least two amino acids that serve to expose the cleavage site to enzymatic or other digestion. This property of the hinge fosters accessibility of the cleavage site to enzymes or other cleavage reagents in the environment of the cleavage reaction and provides a kinetic advantage for preferential digestion at the amino acid residue(s) constituting the cleavage site.

The amino acid sequence comprising the hinge region can vary widely. It often comprises a flexible segment which imparts to the portion of the fused polypeptide about the cleavage site the ability to assume a relaxed, generally unfolded configuration. The combination of amino acids defining the hinge is therefore chosen for its ability to impart specific secondary properties to the portion of the polypeptide it comprises when the fused polypeptide is disposed in the cleavage environment.

The hinge region comprises amino acids which do not form a fixed tertiary conformation which might sterically hinder access of the cleavage agent to its adjacent site of action. For this reason, the hinge for use with the helix typically contains at least one proline residue and is free of cysteine residues. The presence of one or more proline residues substantially precludes the formation of an alpha helical structure in the hinge region. Proline in this case serves to limit the possible static interference to cleavage that may be occasioned by the proximate helical leader. Cysteine, on the other hand, contains a sulfhydryl or thiol group, which is highly reactive and can form disulfide bonds. The presence of cysteine can work against the desired lack of fixed secondary or tertiary conformation of the hinge region, and therefore its use is avoided.

Preferably, the hinge region is a polypeptide chain containing from about two to twenty amino acids. In addition to being cysteine-free and typically containing at least one proline residue, the sequence of the hinge may exploit other design strategies which promote efficient cleavage in the preselected cleavage environment. Particularly when the preselected cleavage agent is an endopeptidase, it is important that the hinge region be soluble in aqueous environments. Amino acids having charged side groups and hydrophilic properties are included in the hinge to promote solubility. These include the anionic residues Glu and Asp, the cationic residues Arg and Lys, and the neutral hydrophilic residues Set and Thr.

Further particulars of the hinge region are disclosed in application Ser. No. 07/462,297, filed Dec. 28, 1989, issued as U.S. Pat. No. 5,013,653 on May 7, 1991, which application is a continuation of U.S. application Ser. No. 07/028,484, filed Mar. 27, 1987, now abandoned, the disclosure of which is incorporated by reference.

The target protein 22' is released from the remaining fusion material preferably in an active form 22" or one which readily reassumes its native conformation as the cleavage site 14' is hydrolyzed by the selected cleavage agent. The specificity of cleavage agents is determined by the identity of the sequence of amino acids at or near the peptide bond which is to be hydrolyzed. A given cleavage agent may recognize the bond between two specific amino acids or may recognize a bond following one or a specific sequence of amino acids.

The specificity of many cleavage agents is known. The table set forth below lists various known cleavage agents and their primary (and in some cases secondary) sites of action.

TABLE 2

| Cleavage Agent | Major Site of Action | Other Sites of Action |
| --- | --- | --- |
| Trypsin | Arg, Lys | |
| Chymotrypsin | Trp, Phe, Tyr | Leu, Met, His |
| Elastase | Neutral Aliphatic Residues | |
| Pepsin | Phe, Leu, Trp | Ala, Gly, Glu |
| Papain | Arg, Lys, Gly | Wide specificity |
| Subtilisin | Aromatic and Aliphatic residues | Various |
| Thermolysin | Amino-linked bonds of Aliphatic Residues | Ala, Phe |
| S. aureus protease | Glu | Asp |

TABLE 2-continued

| Cleavage Agent | Major Site of Action | Other Sites of Action |
| --- | --- | --- |
| Endoproteinase Arg C (Submaxillaris protease) | Arg | |
| Clostripain | Arg | |
| Thrombin | Arg | |
| Collagenase | X—Gly—Pro | X—Ala—Pro X—Gly—Thr |
| Lysobacter enzymogenes (endoproteinase Lys—C) | Lys | |
| Mysobacter Al—1 Protease | Lys | |
| Armillaria mellea | Lys | |
| Flavobacterium meringosepticum | Pro | |
| Factor Xa | Ile—Glu—Gly—Arg | |
| CNBr | Met | |
| BNPS-skatole | Trp | |
| N-bromosuccinimide | Trp | |
| O-iodosobenzoic acid | Trp | |
| HBr/DMSO | Trp | |
| NTCB | Cys | |
| Sodium metal in liquid ammonia | Pro | |
| Hydroxylamine | Asn—Gly | |
| Dilute acid | Asp—Pro | |

Other cleavage agents are known. Those preferred for use int he invention are enzymes with a primary site of action which cleave at the C-terminal side of the cleavage site residue (for hooks attached to the amino side of the target polypeptide) or at the N-terminal side of the cleavage site residue (for hooks attached to the carboxyl side of the target polypeptide). The concurrently most preferred cleavage agent/cleavage site is S. aureus V-8 protease/Glu. When this system is used, Asp should be employed in place of Flu as a C residue in the helix.

The cleavage site in the fused protein generally can comprise any one or sequence of amino acids which can be cleaved by a cleavage agent specific for the site in an appropriate environment. Specificity of cleavage can be increased, and likelihood of undesired cleavage within the target protein or elsewhere in the fused polypeptide can be decreased, by selecting the cleavage agent having a site of action which is absent from the target polypeptide.

The fused polypeptide is preferably cleaved under conditions in which it has assumed its native conformation. This has the effect of masking the presence of potential cleavage sites in the target polypeptide. Being cysteine-free (or having paired Cys residues), the pendant polypeptide remains free of disulfide bonds to extraneous contaminants, and its cleavage site, aided by the hinge, remains open to digestion by the cleavage agent. If cleavage is conducted after the fused polypeptide has been renatured and oxidized, the target polypeptide may be held in its tertiary conformation by one or more disulfide bonds.

The invention is essentially unlimited with respect to the identity of the target protein 22" to be manufactured using the procedures and constructs disclosed herein. Indeed, an important feature of the invention is that it provides a generalized procedure which can be adapted readily to facilitate recombinant production of any desired protein. Thus, this invention may be used to produce growth factors, hormones, lymphokines, enzymes, antibodies or their various fragments including both enzymatically active and inactive proteins, short polypeptides, and various analogs of all of the above. Nonlimiting examples include EGF, IGF-1, TGF alpha and beta, human collaginase inhibitor, PDGF, CTAP, interleukins, interferons, industrial enzymes, thrombolytic agents, vital envelope proteins, bacterial membrane proteins, protein A and its fragments, and various synthetic peptides.

Figure 4:
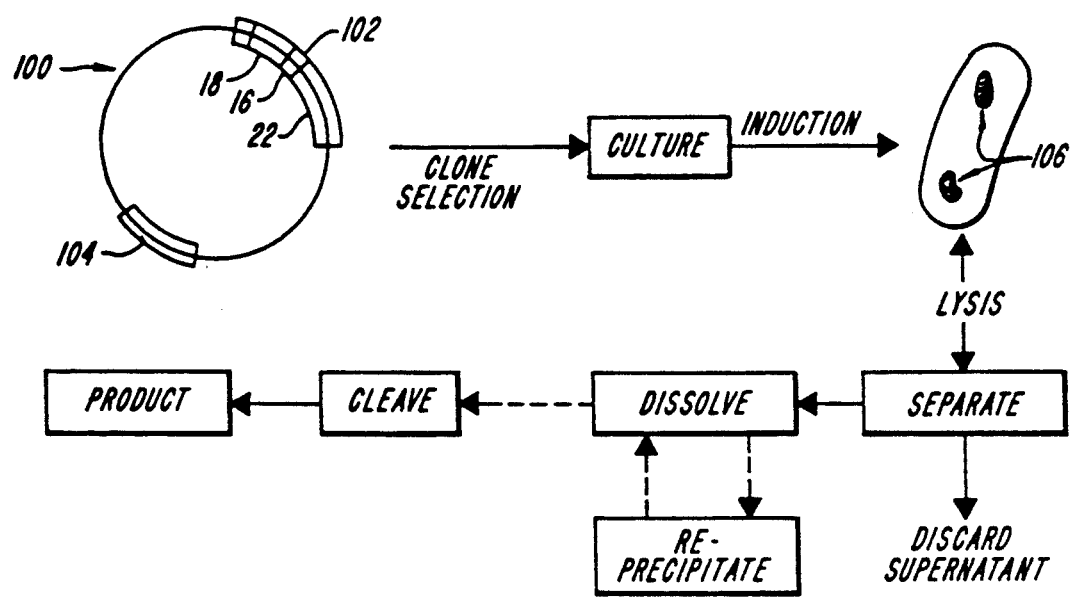
FIG. 4 is a schematic illustration of the overall process of the invention.

The overall process for protein production conducted in accordance with the invention is schematically illustrated in FIG. 4. The amphiphilic helix and other recombinant DNA constituting the cleavage site and hinge region, appropriate regulatory sequences, and the gene encoding the target polypeptide are constructed using any of a large variety of known techniques of the type outlined above. After assembly of the DNA, an expression vector is constructed, again using conventional techniques, designed for incorporation into a suitable host cell, such as E. coli.

The expression vector (100 in FIG. 4) will typically comprise a transcription unit 102 corresponding to the DNA of FIG. 3 and a marker gene 104 which imparts to the host cell a phenotypic characteristic which enables selection of successfully transformed clones. Clones expressing the fused protein are then cultured in mass to produce a large population of cells containing intracellular inclusion bodies (106 in FIG. 4). The cells are then lysed by conventional techniques, and the inclusion bodies are collected, e.g., by centrifugation. After separation of the inclusion bodies from soluble proteins in the supernatant, the inclusion bodies may be redissolved by exposure to a solution having an appropriate ionic strength and/or pH designed to dissociate the aggregates of the amphiphilic helix with its attached target protein generally as discussed above. In some cases, these dissolved inclusion bodies may be cleaved without additional purification, and the cleavage fragments may be separated to harvest the product of interest. Alternatively, the fused protein may be subjected to a series of solubilization and precipitation procedures designed to separate contaminants having solubility properties differing from the unique properties of the helix. The purified inclusion bodies are then subjected to cleavage to yield product.

If a potential cleavage site happens to be present in the amino acid sequence of the target polypeptide, the design of the pendant polypeptide as disclosed above favors cleavage at site 14'. In such circumstances, if the reaction is allowed to go to completion, both sites may be cleaved, with the result that little or no intact target polypeptide is harvested.

In this case, the cleavage reaction may be terminated before completion, the target polypeptide removed from the reaction mixture, and the remainder of the fused polypeptide again subjected to cleavage or, in effect, recycled. This strategy can reduce loss of target polypeptide by removing it from the reaction before the protease attacks the second, less reactive cleavage site. Further particulars of this recycle cleavage procedure are disclosed in copending U.S. application Ser. No. 07/899,237, filed Jun. 16, 1992, which is a continuation of U.S. application Ser. No. 07/746,281, filed Sep. 2, 1991, now abandoned, which is a continuation of U.S. application Ser. No. 07/028,483, filed Mar. 20, 1987, now abandoned. the disclosure of which is incorporated herein by reference.

Alternatively, cleavage of the target polypeptide may be eliminated by altering its amino acid sequence at the DNA level to replace residues in its structure which may be subject to cleavage with chemically similar residues which, under the conditions of the cleavage reaction, are not cleaved. A similar strategy can avoid unwanted cleavage of the amphiphilic helix. Thus, where S. aureus V-8 protease is the preselected cleavage agent, Glu residues should not be used as a charged residue (C) in the structure of the helix. The cleavage reaction is then conducted under conditions in which the S. aureus V-8 protease cleaves at a Glu residue and does not cleave, or cleaves at a slower rate, at an Asp residue. For example, alkaline media, e.g., pH about 8.0, and the presence of acetate or carbonate ion, promotes Glu cleavage and minimizes Asp cleavage. When employing this amino acid replacement technique, it is often not necessary to replace all of the potential cleavage sites in the target protein, as in many cases they will be inaccessable to endoprotease hydrolysis because of the stereochemistry of the renatured target proteins.

The following examples more fully illustrate preferred features of the invention.

EXAMPLES

In the design of an amphiphilic helix useful in the production of relatively short target polypeptides such as human epidermal growth factor and calcitonin, a series of prototype amphiphilic helices were constructed for evaluation by synthesizing oligonucleotides and ligating them together to produce the recombinant DNAs encoding the proteins set forth below.

|      | N   C   S   N   S   C   N |
|------|---------------------------|
| Ah5A | (GCT AAA AAT CTT AAT GAA GCT)₅ |
|      | (Ala—Lys—Asn—Leu—Asn—Glu—Ala)₅ |
| Ah4A | (GCT AAA AAT CTT AAT GAA GCT)₄ |
|      | (Ala—Lys—Asn—Leu—Asn—Glu—Ala)₄ |
| Ah3B | (GCT AAA CAA CTT CAT GAT GCT)₃ |
|      | (Ala—Lys—Gln—Leu—His—Asp—Ala)₃ |
| Ah5B | (GCT AAA CAA CTT CAT GAT GCT)₅ |
|      | (Ala—Lys—Gln—Leu—His—Asp—Ala)₅ |

The DNA coding sequence for the Ah4A and Ah5A leaders was created by synthesizing overlapping, complementary DNA fragments of 15 bases each using phosphoramidite chemistry. Internal fragments were phosphorylated (phosphate added to the 5' OH) while end fragments were left unphosphorylated so as to prevent polymerization of gene segments during the ligation of the fragments. The left (amino-terminal) end of the synthetic gene was left with EcoR I sticky ends while the right hand end typically had BamH I sticky ends.

The DNA coding sequence for the Ah3B leader was created by synthesizing two complementary DNA fragments of 74 bases each using phosphoramidite chemistry in a Biosearch oligonucleotide synthesizer. In designing the nucleotide sequence of the helical region, the possible codons for the amino acid sequence Ala Lys make possible the inclusion of an Esp I restriction site at such locations in the sequence. This site is very useful for future modifications of the gene because it is highly specific and absent in the cloning vector used, pUC8 (Viera and Messing (1982). Gene 19:259). Consequently, a single Esp I site was included at the beginning of the coding region for the third helix segment. Subsequently, the coding sequence for the Ah5B helix was formed by synthesizing the DNA for a model B dimer having Esp I ends which was then inserted into the sequence for the Ah3B leader by cutting that DNA sequence at the unique Esp I site.

The synthetic DNA was cloned using the linker mutagenesis method. The DNA for the initial Ah3B coding sequence was made such that, when dimerized to form a double helix, overlapping ends were left that were compatible with an initial Nco I restriction site and a terminal BamH I site. The synthetic DNA was cloned into a pUC plasmid containing these sites and an EcoR I proximal to the Nco I site. Both the Ah3B and Ah5B coding regions could then be moved in ahead of several pre-existing EGF genes with cleavage sites to form leader-cleavage site-EGF constructs.

An alternative approach to creating the DNA coding sequence for a series of helix multimer regions is to synthesize three sets of DNA regions: one coding for the first helical segment including the initial Met codon (ATG) and a leftward flanking restriction site for cloning, one set coding for one internal segment (e.g., from Ala to Ala) and one set coding for the last helical segment with a rightward flanking restriction site for the connection of the DNA for the helix to the DNA for the cleavage site and target protein gene. The ends of the DNA segments are designed such that complementary 5' overhanging ends are left that cover the Ala Ala region between helical segments. By varying the relative amounts of DNA coding for the end segments and internal segments, the length of helical polymer DNA created during ligation of the fragments can be controlled. The actual size of resulting clones is determined by sequencing at the DNA level.

As can be appreciated from the foregoing list of helix structures, Ah5A employed Asn as side amino acids, Leu and Ala as nonpolar amino acids, Lys as a cationic amino acid, and Glu as an anionic amino acid such that each segment of the 5 segment oligomer had no net charge. Sequencing of the expressed polypeptide indicated that the Glu residue in the fourth segment and the second Ash residue in the fifth segment had been replaced during the synthesis by Lys and Set residues, respectively. Helix Ah4A was identical to Ah5A except that only 4 repeating units were used. Sequencing revealed that the first Ala residue of the first segment had been replaced during synthesis by Val. Helix Ah3B employed 3 repeating units and Ah5B employed 5 repeating units wherein His was used as a side amino acid, Asp replaced Glu, and Gln replaced Ash in the structure of the Ah5A and Ah4A helices.

Helix Ah5A was expressed as a fusion protein having the following amino acid sequence:

Met-(Ah5A)-Asp-Pro-Pro-Pro-Glu-Leu-Arg-Arg-(EGF)

wherein EGF is the amino acid sequence of human epidermal growth factor, Asp-Pro-Pro-Pro-Glu served as the hinge, and the Leu-Arg-Arg sequence comprised a cleavage site accessible to trypsin digestion at pH 8 in 1 M urea. This fusion protein, upon expression, readily formed inclusion bodies which constituted 25% of the total cellular protein and 80% of the insoluble protein. As theory would predict, the fused protein exhibited no significant change in solubility with variation in pH.

The frozen cells containing the inclusion bodies were suspended in a wash solution (25% sucrose, 25 mM Tris, pH 8, and 10 mM EDTA) at a concentration of approximately 100 mg/ml. The cells were then centrifuged, and the pellet was resuspended in the solution described above plus 1% detergent (sodium dodecyl sulphate), and maintained at 0° C for 30 minutes. After centrifugation, the cell pellet was washed again in the wash solution to remove the detergent, centrifuged, resuspended in the Tris-EDTA buffer plus 0.01% lysozyme, frozen and thawed once, and then sonicated twice for 30 seconds on ice. The inclusion bodies and cell debris were again separated by centrifugation, and the pellet was resuspended in 6 M urea, 20 mM Tris, pH 8 to dissolve the inclusion bodies. The remaining solid was separated by centrifugation, and the supernatant containing dissolved fused protein was diluted with urea to a final concentration of 1 M.

Samples of the solubilized protein were then digested with trypsin (2 ug/ml and 10 ug/ml) for both 15 minutes and one hour. The digest with the lower protease concentration for 15 minutes produced 100% cleavage of the EGF fusion protein. Five C-terminal amino acids of the EGF were also partially cleaved in this reaction.

In a second experiment, the inclusion bodies were prepared and cleaved as set forth above, except that 1% CHAPS buffer (3[(3-chloramidopropyl) dimethyl ammonio]-propanesulfonate) was added before sonication. The digestion products were separated on polyacrylamide gels. Immunoblotting treatment with EGF antibody demonstrated that a digestion fragment of the approximate correct molecular weight for EGF had been produced. Higher molecular weight contaminants and digestion fragments can be removed from the EGF product readily on a C18 column, loading and washing with 10% $CH_3CN$, and eluting with 60% $CH_3CN$.

A fused polypeptide similar to that described above but employing Ah4A as the amphiphilic helix was then expressed in the hope that four repeating units of the helical structure would prove less refractory to solubilization. The fusion protein had the structure:

Met-(AH4A)-Asp-Pro-Leu-Pro-Glu-Leu-Ser-Arg-EGF

In this construct, the Pro-Leu-Pro tripeptide in the hinge increased accessibility of trypsin to the arginine cleavage site.

This modified fusion protein, upon expression, readily formed inclusion bodies which constituted 20% of the total cellular protein and was soluble in media of moderate ionic strength. Consequently, it could be successfully cleaved by trypsin in 1M urea at pH 8.

The inclusion bodies were prepared as described above except that 25 mg/ml cells were used and CHAPS buffer (10 mM) was used instead of sodium dodecyl sulfate in the second step. The fused polypeptide, as expected, was more soluble than the Ah5A construct, and a stronger detergent prewash resulted in significant loss of product. As a result, the inclusion bodies contained more contaminants, some of which could be removed with solvents such as dimethylsulphoxide and 0.1 M acetic acid.

Protein from inclusion bodies solubilized in 1 M urea, 2 mM Tris, pH 8, 0.1 mM EDTA was either digested directly or was purified by elution from phenylsilica with 30% $CH_3CN$ and 5 mM borate buffer, pH 8-9. Digestions were conducted at 37° C. for 3 or 10 minutes using 100, 10, 1.0, and 0.1 ug/ml trypsin (pH 8). Digestion with 1 ug/ml trypsin for 3 minutes was clearly enough to cleave over half the silica purified material.

The Ah3B amphiphilic helix was expressed as a fusion protein having the following sequence:

ShLE-Met-(Ah3B)-Asp-Pro-Asp-Pro-Asp-Ala-Ala-Ile-Glu-Gly-Arg-EGF wherein ShLE is the short trp leader sequence (Met-Lys-Ala-Ile-Phe-Val-Seu-Lys-Gly-Ser-Leu-Asp-Arg Asp-Leu-Glu-Phe), the Asp-Pro-Asp-Pro-Asp-Ala-Ala sequence comprised the hinge, and the Ile-Glu-Gly-Arg sequence is a recognition site for factor Xa cleavage.

With a trisegment helix leader section, inclusion bodies were not formed unless the Trp leader comprised part of the construct. The Ah5B leader constructs did produce intracellular inclusion bodies whether or not attached to the ShLE leader. Protein was recovered by washing the cells with 25% sucrose, 25 mM Tris, 10 mM EDTA, and 100 mM NaCl for one hour at 0° C. The cells were then centrifuged, washed once with 5 mM Tris, 2 mM EDTA, frozen, thawed, brought to 10 mM in EDTA, mixed with 0.01% lysozyme, sonicated over ice for 30 seconds, and recentrifuged to collect the inclusion bodies.

The inclusion bodies were dissolved in 8M urea and gel sample buffer, and the resulting solution was loaded onto a 15% polyacrylamide gel. The construct band was cut out and the protein passively eluted in water at room temperature for 16 hours. Neat beta-mercaptoethanol (BME) was added to the solution to result in a concentration of 0.1%, sufficient urea to bring the concentration to 2 M, and sufficient sodium cholate to bring the concentration to 0.1%. This solution was then dialyzed against, a) 5 mM Tris, pH 7.5, 0.1% sodium cholate, 2 M urea, 1 mM reduced glutathione, and 100 mM oxidized glutathione; b) the same solution without sodium cholate; c) the same solution without sodium cholate or urea; and d) 50 mM Tris pH 8.4.

Cleavage was conducted in 14 ul volumes with about 1 ug protein/50 mM Tris, pH 8, 5 mM Ca++ and 7.5 uU, 75 uU and 750 uU Factor Xa for one hour at 37° C. At the lower Factor Xa concentrations, distinct bands of intact EGF are produced.

To further evaluate amphiphilic helix structures with respect to their solubility characteristics, the following synthetic dimers were prepared using a Biosearch solid phase peptide synthesizer.

|      | N | C | S | N | S | C | N |
|------|---|---|---|---|---|---|---|
| P-72 | (Ala—Lys—Asn—Leu—Asn—Glu—Ala)$_2$ | | | | | | |
| P-81 | (Ala—His—Asn—Leu—Asn—Glu—Ala)$_2$ | | | | | | |
| P-87 | (Ala—Lys—Gln—His—Gln—Glu—Ala)$_2$ | | | | | | |

Helix P-72 consisted of the dimeric form of helix Ah5A. Helix P-S1 also comprised the dimeric form of helix Ah5A. Each unit was identical to Ah5A except that His replaced the cationic Lys residue as a charged amino acid. P-87 also comprised two repeating units similar to Ah5A, except that Gln was used as the side amino acid residues in place of Asn, and the central nonpolar Leu residue of Ah5A was replaced by His.

The three synthetic peptide dimers are expected to interact with nonpolar phases differently under different solution conditions.

Dimer P-72 carries a net charge of zero and contains no groups that titrate in the pH range around neutrality; it is expected, therefore, that P-72 will aggregate or interact with nonpolar phases in a manner that is independent of pH.

Peptide P-S1, on the other hand, carries a net zero charge at low pH (below 7) when the His is charged, but becomes negatively charged at high pH when the His loses its charge. Consequently, P-S1 is expected to interact with a nonpolar phase more strongly at low pH than at high pH. Conversely, peptide P-87, which is expected to be positively charged at low pH and neutral at high pH, is expected to interact with a nonpolar phase more strongly at high pH when the His has titrated and is neutral. Because the intracellular pH of E. coli is about 7.6, P-87 is expected to aggregate under physiological conditions. In addition, because the His is located within the nonpolar region, when the His is charged, nonpolar aggregation interactions should be strongly inhibited.

To determine whether the properties of the synthetic helices corresponded to their expected properties, each was tested on an HPLC column using a nonpolar (C-18) stationary phase.

A sample of synthetic peptide solution was then injected, and the elution time (time to emerge from the bottom of the column) measured. The void time for the column was measured by injecting a small charged molecule such as citrate or acetate. The fraction of the sample solubilized in the aqueous, mobile phase (versus that bound to the hydrophobic, immobile phase) is determined by the void time divided by the sample elution time. A sample emerging in the void time is completely soluble in the mobile phase, whereas if it emerges in two void times it is half solubilized in the mobile phase and half bound to the stationary phase. By this procedure the affinity of each of the synthetic peptides for the aqueous, mobile phase, relative to the hydrophobic, stationary phase, could be measured as a function of pH.

The HPLC column was run isocratically (constant eluent) using one of several different buffer systems. The elution times for the synthetic peptides are highly sensitive to the concentration of acetonitrile used. For that reason a value of 13% was used for all the buffer systems in that at that concentration the elution time for the peptides was determined to be on the order of 2 to 20 times the void time. The running pH of the particular buffer system used was adjusted by varying the ratio of solutions A and B, where solution A was at low pH, and solution B was set at high pH. The column was allowed to equilibrate as judged by 214 nm absorbance baseline stability. Equilibration times varied up to several hours in some cases, especially where the pH buffering capacity of the buffer system was low.

The buffer systems used were as follows: for the pH range 6.8 to 8.0:10 mM phosphate with 10 mM sodium ion in A and 20 mM sodium ion in B; for the pH range 4.0 to 5.5:10 mM acetate with 5.3 mM sodium ion in A and 9.5 mM sodium ion in B; for the pH range 4.0 to 8.0:10 mM phosphate, 10 mM acetate with 0 mM sodium ion in A and 20 mM sodium ion in B; for the pH range 6.0 to 9.0:5 mM phosphate, 5 mM pyrophosphate with 10 mM sodium ion in A and 20 mM sodium ion in B; for the pH range 4.0 to 10.0:5 mM phosphate, 5 mM pyrophosphate, 20 mM sodium ion with 12 mM acetate ion in A and 0.8 mM acetate ion in B. Because the concentrations of charged ions must be varied in order to vary pH, there is with the change in pH a concomitant change in the ionic strength of the mobile phase in these buffer systems. In those systems where the cation is varied, the ionic strength increases with increasing pH, whereas in the system where the anion was varied, the ionic strength decreases with increasing pH.

Figure 5:
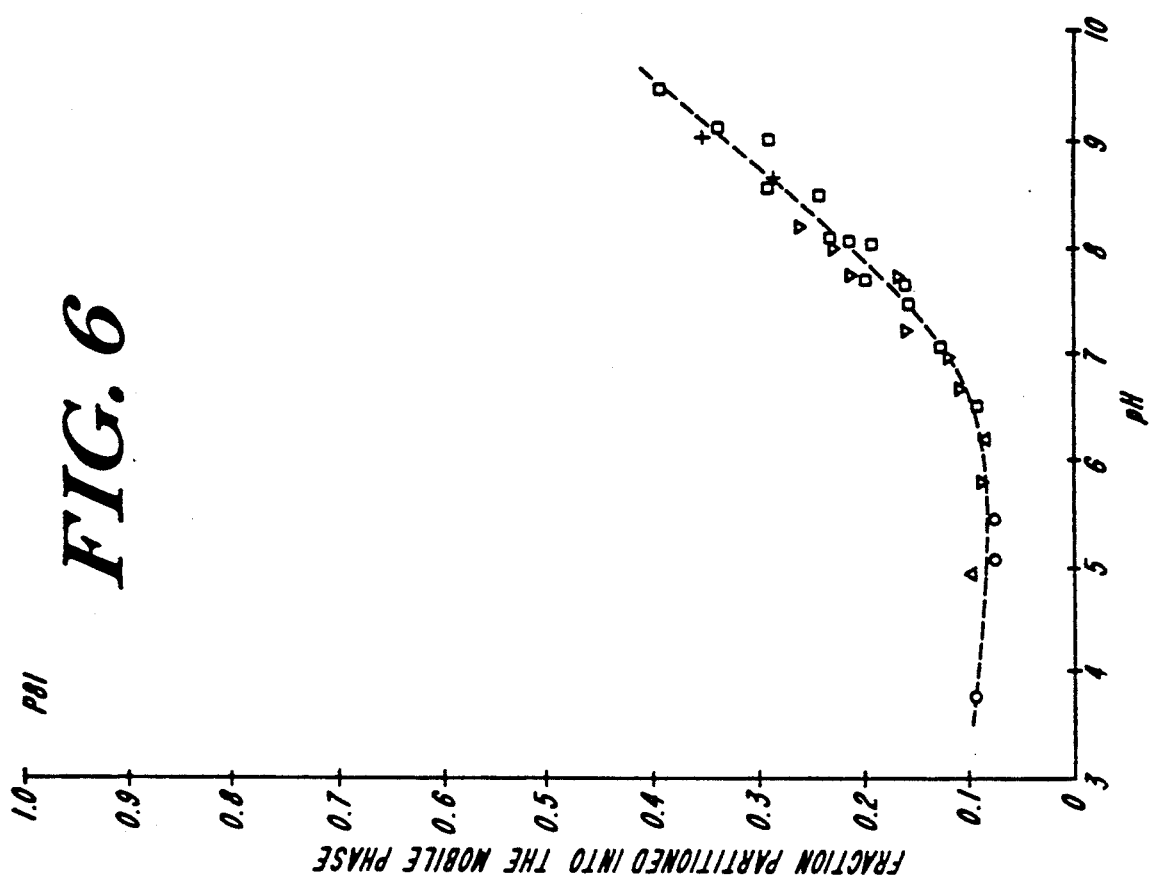
FIGS. 5, 6, and 7 are graphs of the solubility of the three prototype helices, respectively, helix P-72, helix P-81, and helix P-87, as a function of pH, where solubility is expressed as the fraction of peptide partitioned into the aqueous, mobile phase of an HPLC hydrophobic media column. This illustrates the effect of pH on the solubility properties of the particular helices. In these graphs the point symbols correspond to the following buffer systems used.

FIG. 5 shows the results of these experiments on the P-72 peptide dimer containing no histidine. The graph illustrates variation in the partition coefficient, which is indicative of the fraction of the helix partitioned into the mobile phase, as a function of pH. As illustrated, as the pH increased the peptide partitioned increasingly into the hydrophobic (stationary) phase. Such an effect is not expected for this peptide as it contains no amino acid residues that titrate in the pH range of the experiment. The effect may be due to the fact that the ionic strength of the buffer systems used increases some what with increasing pH, thereby increasing hydrophobic interactions between the helix and the hydrophobic stationary phase.

Figure 6:
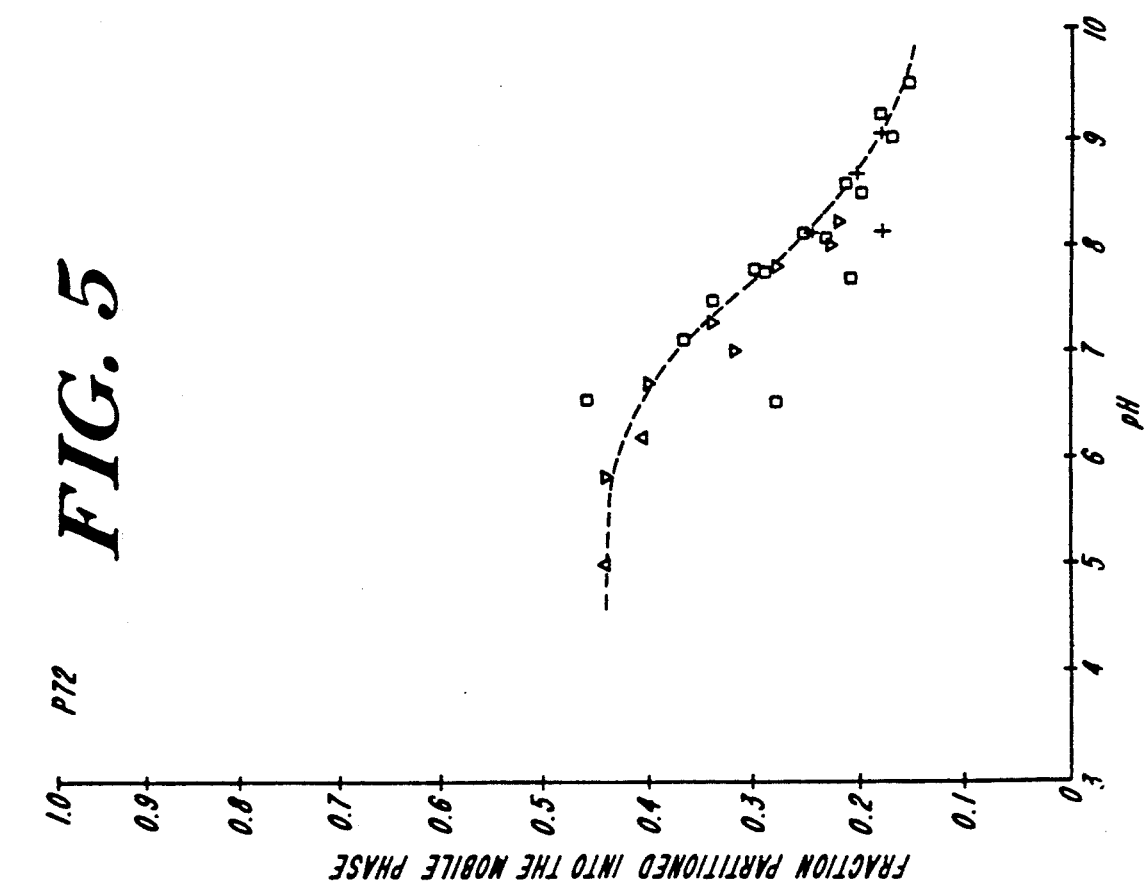

FIG. 6 displays the data for helix P-81 containing histidine. The data demonstrate that the fraction of the helix partitioning into the mobile phase increases as pH increases. This is consistent with the expected results because at increased pH, P-81 would be expected to have a net negative charge, and thus have affinity for the aqueous mobile phase relative to the nonpolar stationary phase.

Figure 7:
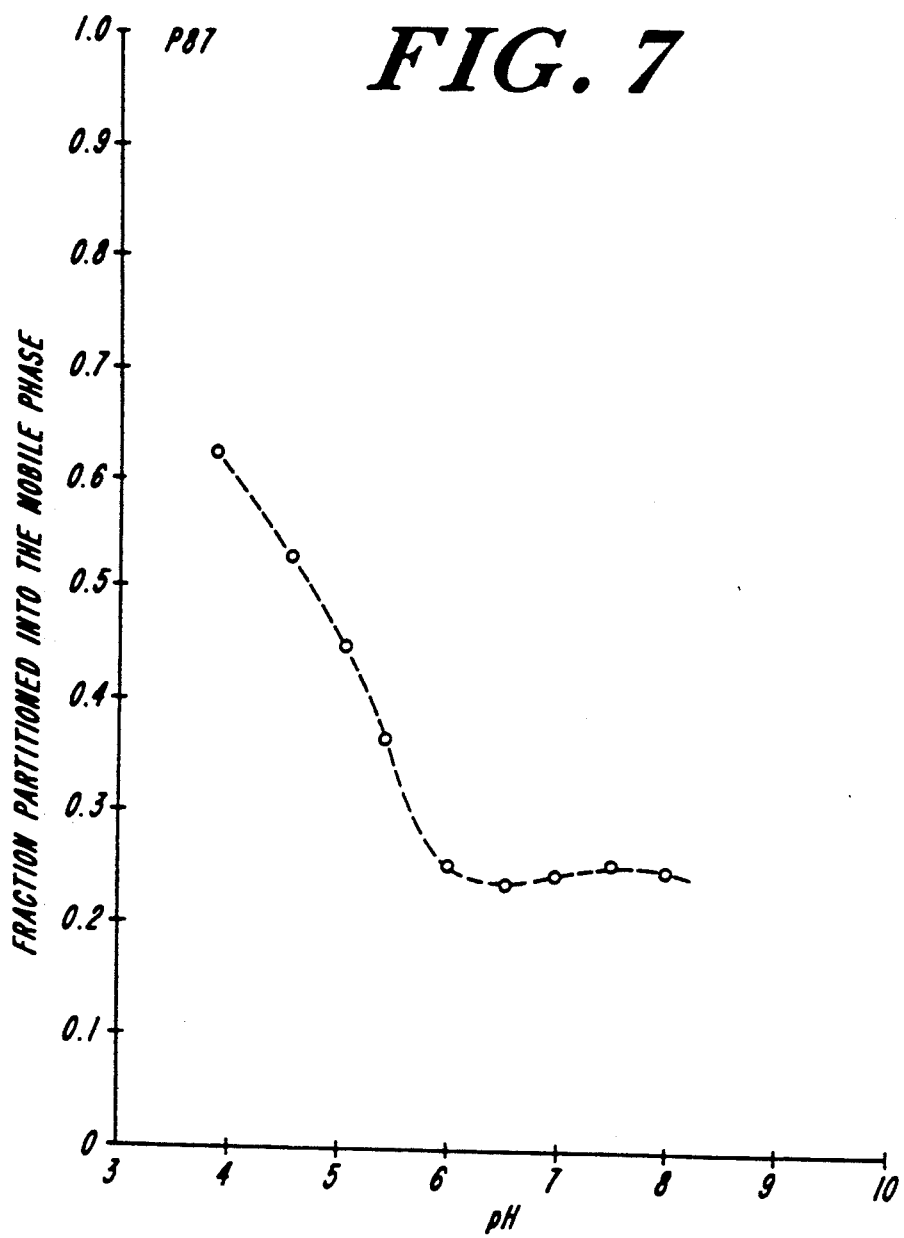

FIG. 7 illustrates the results of these experiments using helix P-87. As illustrated, and consistent with predicted behavior, when the histidine residue was charged at low pH the helical dimer had a high affinity for ionic media (mobile phase), whereas above about pH 6.5, a relative low, substantially constant affinity for ionic media is observed.

In a separate experiment, the change in the amount of light scattered by solutions of the synthetic peptides at 90° to the incident beam was used to follow changes in the degree of self-aggregation as a result of changes in the pH and ionic strength. Scattered light was observed using a Perkin-Elmer LS5 luminescence spectrophotometer with both the excitation and emission monochromators tuned to a wavelength of 300 nm. Each peptide was disposed in distilled water and increasing concentrations, alternately, of acetic acid and sodium hydroxide, were added so as to alternate between acid and basic conditions. The results of these titrations are set forth in Table A below. The values therein reflect the amount of light scattered by the solution relative to that scattered by the solvent under the same conditions.

TABLE A
LIGHT SCATTERING RESULTS

| | | | Sample | | | | | |
|---|---|---|---|---|---|---|---|---|
| | | w¹ | P-81 | | | P-87 | | |
| Added | pH | (mM) | S² | Δp³ | ΔO⁴ | S | Δp | ΔO |
| A Sample | 7.0 | 0 | 0.86 | | | 3.6 | | |
| B HAc | 3.0 | 1 | 0.60 | + | − | 2.5 | − | − |
| C NH₄OH | 8.4 | 45 | 0.36 | − | − | 3.0 | + | + |
| D HOAc | 5.1 | 49 | 0.84 | + | + | 1.5 | − | − |
| E NH₄OH | 8.4 | 69 | 0.41 | − | − | 1.8 | + | + |
| F HAc | 5.1 | 74 | 0.16 | + | − | 1.2 | − | − |

¹ionic strength of the solution
²relative 90 degree scattering signal
³predicted change in scattering
⁴observed change in scattering As can be seen from the data for P-81, when the pH drops below neutrality, where the peptide is expected to carry zero net charge and to tend to aggregate, an increase in scattering is seen in one instance. Conversely, when the pH rises above neutrality, where the peptide is expected to carry a negative net charge and to dissociate, a decrease in scattering is seen. P-87, on the other hand, carries an extra charge and is expected to behave just the opposite of P-81. The scattering changes from solutions of P-87 vary in the predicted manner.

The invention may be embodied in other specific forms without departing from the spirit and scope thereof.

Accordingly, other embodiments are within the following claims.

What is claimed is:

1. A method of promoting the formation of inclusion bodies comprising a target polypeptide within a cellular host which expresses said target polypeptide, said method comprising the steps of:
    ligating in reading sequence a pendant DNA to a DNA encoding said target polypeptide to produce a fused DNA, said pendant DNA comprising a sequence of nucleotides which encodes a proline-free alpha helical polypeptide having a central axis and opposed hydrophilic and hydrophobic lateral surfaces, the hydrophobic surface comprising axially proximate nonpolar amino acid residues, the hydrophilic surface comprising axially proximate charged amino acid residues, said alpha helical polypeptide being of the structure:
    (N—C—S—N—S—CN)b
    wherein b is an integer from 1 to 30, N comprises a member selected from the group consisting of nonpolar amino acid residues, and the Ns together define said hydrophobic surface, C comprises a member selected from the group consisting of charged amino acid residues, and the Cs together define said hydrophilic surface, S comprises a member selected from the group consisting of hydrophilic, neutral amino acid residues, and wherein up to two of said N, C and S residues can independently be histidine, said alpha helical polypeptide being further characterized by formation of insoluble aggregates within said cellular host; and
    expressing said fused DNA in said cellular host to produce insoluble aggregates comprising a fused protein encoded by said fused DNA.

2. The method of claim 1 wherein N is selected from the group consisting of phenylalanine, leucine, isoleucine, valine, alanine, tryptophan, and methionine.

3. The method of claim 1 wherein C is selected from the group consisting of aspattic acid, glutamic acid, and lysine.

4. The method of claim 1 wherein S is selected from the group consisting of asparagine and glutamine.

5. The method of claim 1 wherein one of said C's is selected from the group consisting of aspattic acid and glutamic acid and the other of said C's is lysine, whereby one of said C's is a cationic amino acid residue and the other is an anionic amino acid residue.

6. The method of claim 1 wherein the target polypeptide comprises amino acid residues collectively imparting a net charge of a first polarity and wherein C consists of amino acid residues imparting a net charge to the pendant polypeptide opposite that of said first polarity.

7. The method of claim 1 wherein at least one of said N's is histidine.

8. The method of claim 1 wherein at least one of said C's is histidine.

9. The method of claim 1 wherein at least one of said S's is histidine.

10. The method of claim 1 wherein said insoluble aggregates comprising said fused protein represent at least about 10% by weight of the total expressed protein of the cellular host.

* * * * *

UNITED STATES PATENT AND TRADEMARK OFFICE
CERTIFICATE OF CORRECTION

PATENT NO. : 5,330,902
DATED : July 19, 1994
INVENTOR(S) : Keck et al.

It is certified that error appears in the above-indentified patent and that said Letters Patent is hereby corrected as shown below:

Column 18, line 43,
Claim 3, line 2, change "aspattic" to --aspartic--.
Claim 5, line 2, change "aspattic" to --aspartic--.

Signed and Sealed this

Twenty-ninth Day of November, 1994

Attest:

BRUCE LEHMAN

*Attesting Officer*    Commissioner of Patents and Trademarks